(12) United States Patent
See

(10) Patent No.: US 6,979,296 B2
(45) Date of Patent: Dec. 27, 2005

(54) METHODS FOR ULTRASONIC IMAGING AND TREATING DISEASED TISSUES

(75) Inventor: Jacko R. See, Fullerton, CA (US)

(73) Assignee: SBM Biologics, Inc., Cupertino, CA (US)

( * ) Notice: Subject to any disclaimer, the term of this patent is extended or adjusted under 35 U.S.C. 154(b) by 132 days.

(21) Appl. No.: 10/406,748

(22) Filed: Apr. 3, 2003

(65) Prior Publication Data

US 2004/0030252 A1 Feb. 12, 2004

Related U.S. Application Data

(60) Provisional application No. 60/369,786, filed on Apr. 3, 2002.

(51) Int. Cl.[7] .................................................. A61B 8/14
(52) U.S. Cl. ..................................................... 600/458
(58) Field of Search ........................ 600/439, 459–472, 600/458; 424/9.51, 9.92, 85.1

(56) References Cited

U.S. PATENT DOCUMENTS

| | | | |
|---|---|---|---|
| 4,235,871 A | | 11/1980 | Papahadjopoulos et al. |
| 5,469,854 A | * | 11/1995 | Unger et al. ................ 600/458 |
| 5,536,489 A | * | 7/1996 | Lohrmann et al. .......... 424/9.52 |
| 5,716,597 A | * | 2/1998 | Lohrmann et al. .......... 600/458 |
| 5,935,553 A | * | 8/1999 | Unger et al. ................ 424/9.51 |
| 5,935,598 A | * | 8/1999 | Sage et al. .................. 424/449 |
| 6,030,603 A | * | 2/2000 | Lohrmann et al. .......... 424/9.52 |
| 6,120,751 A | | 9/2000 | Unger |
| 6,200,960 B1 | | 3/2001 | Khachigian |
| 6,331,289 B1 | | 12/2001 | Klaveness et al. |
| 6,444,192 B1 | * | 9/2002 | Mattrey ...................... 424/9.52 |
| 6,495,129 B1 | * | 12/2002 | Li et al. ..................... 424/85.1 |
| 6,733,451 B2 | * | 5/2004 | Rabiner et al. ............. 600/439 |

OTHER PUBLICATIONS

Childers et al., "Oral Immunization of Humans with Dehydrated Liposomes Containing Streptococcus Mutans Glucosyltransferase Induces Salivary Immunoglobulin $A_2$ Antibody Responses," Oral Microbiology and Immunology, vol. 9, No. 3, Jun. 1994, pp. 146-153.

* cited by examiner

*Primary Examiner*—Ali Imam
(74) *Attorney, Agent, or Firm*—Christie, Parker & Hale, LLP

(57) ABSTRACT

A method for imaging diseased tissue is provided. The method provides delivering to the diseased tissue a liposomal imaging agent comprising liposomes containing an imaging agent. The liposomal imaging agent is bound to an antibody by an antigenic linker so that the antibody binds the liposomal imaging agent to the diseased tissue. The liposomes are broken to release the imaging agent using a catheter, and the imaging agent is viewed using an imaging technique. The tissue can also be treated by delivering a therapeutic agent to the tissue using the catheter, for example, within the liposomes of the liposomal imaging agent.

16 Claims, No Drawings

METHODS FOR ULTRASONIC IMAGING AND TREATING DISEASED TISSUES

CROSS-REFERENCE TO RELATED APPLICATION

This application claims priority of U.S. Provisional Application No. 60/369,786, filed Apr. 3, 2002, the entire disclosure of which is incorporated herein by reference.

BACKGROUND OF THE INVENTION

The therapeutic use of antibodies has been recently approved. In fact, therapeutic imaging targets can be reached without allergic reactions. However, such procedures involve the intravenous injection of antibodies, which circulate throughout the body and hopefully attached to an antigen of a tumor, infection or site of scarring.

However, the ability to concentrate enough antibody at the target site is a problem. Antibodies are quite large molecules of complex, folded sequences of amino acids that have difficulty in penetrating the diseased tissue. The leakiness and varied vascularization and intralesional pressure of each type of tumor, infection or area of scarring due to ischemia will limit the application of antibody therapies. Antibodies that are hooked or linked to contrast imaging agents make an even larger molecule, which the further complicates the problem of penetration of the imaging or therapeutic agent into the tissue to be treated, i.e., target tissue. This problem results irrespective of whether the imaging agent is an isotope, a PET, an MRI, or a CT-type imaging agent. Further, this problem exists despite the different leakiness of different diseased tissues due to different disease entities.

With the advent of pulse inversion imaging, double resonance ultrasound imaging, and dual harmonic echo Doppler imaging, as well as 3-dimensional reconstruction, areas of imaging throughout the body for diagnosis and treatment can be satisfactorily obtained simultaneously if a contrast agent is use. Such ultrasound contrast agents typically contain an air or gas infiltrate core to increase reflectance of the diseased tissue to be studied.

DESCRIPTION OF THE INVENTION

The present invention is directed to methods for imaging and treating diseased tissue, including tumors, areas of infection, areas of infarction, areas of scarring, and areas of degeneration or tissue overgrowth of unknown etiology. In accordance with the invention, a catheter delivery system is used to deliver a liposomal ultrasound imaging agent directly into the area of interest.

Ultrasound imaging catheters are generally known in the art. In accordance with the invention, the catheter has an ultrasound device, e.g., a piezoelectric device, mounted near its distal end. A lumen passes through the length of the catheter and is open at its distal end for introduction of the imaging agent and other agents into the patient's body, discussed further below. The lumen is preferably sufficiently large to permit the passage of a moveable guidewire through the lumen for introduction of the catheter into the patient's body. The catheter preferably also includes an electrode capable of delivering radio frequency energy or other suitable energy, as discussed further below. The electrode is preferably a tip electrode mounted at the very distal end of the catheter, but alternatively could be a ring electrode or have any other suitable design.

The liposomal imaging agent preferably comprises gas-filled liposomes. A preferred method for making gas-filled liposomes involves using known agents to first make liquid liposomes. The liposomes are repeatedly frozen and thawed to induce the inner retentate to go directly from the solid state to the gaseous state while the outer layers of the liposome do not. Lyophilization is repeatedly used in cycles to aerosolize the inner portion while keeping the outer layers intact. Preferred gases for incorporation into the liposomes include air, oxygen, hydrogen, nitrogen, fluorocarbons, argon, xenon, helium, and fluoropropanes.

The liposomes of the present invention may be made of any suitable phospholipid, glycolipid, derived lipid, or the like. Examples of suitable phospholipids include phosphatidyl choline, phosphatidyl serine, phosphatidic acid, phosphatidyl glycerin, phosphatidyl ethanolamine, phosphatidyl inositol, sphingomyelin, dicetyl phosphate, lysophosphatidyl choline and mixtures thereof, such as soybean phospholipids, and egg yolk phospholipids. Suitable glycolipids include cerebroside, sulphur-containing lipids, ganglioside and the like. Suitable derived lipids include cholic acid, deoxycholic acid, and the like. The liposomes may be formed by any of the known methods for forming liposomes and may be loaded with an agent according to known procedures. Known methods for forming liposome-encapsulated agents are described, for example, in U.S. Pat. No. 4,235,871 to Papahadjopoulos, et al., and Oral Microbiology and Immunology, 1994, 9:146–153, the disclosures of which are incorporated herein by reference.

After the imaging agent is delivered with the catheter, the ultrasound imaging agent can be imaged to assure that it is in the desired location, e.g., just outside a tumor that has increased core pressure and dense capillary networks that do now allow therapeutic agent into it, utilizing the same catheter in the same position. If the imaging agent is the desired location, in the case of imaging agent encapsulated within liposomes, the catheter can be used to burst the liposomes to release the imaging agent, for example, using radio frequency or ultrasound energy. Other types of energy that can be used in connection with the invention include visible light, microwave energy, ultraviolet or infrared light having a wavelength of about 200 to about 1000 nm, laser energy and electromagnetic energy. Energy can also be delivered directly into the tumor or other target site to make the target more leaky, thus allowing more imaging agent into the target site. Preferably the energy is applied at a frequency ranging from 0.5 kHz to 40 kHz and an amplitude ranging from about 150 $\mu$m to 500 $\mu$m. Different amounts and types of energy can be used depending on the particular application. For example, one frequency of dual resonance imaging can be used to track the liposomal bubbles (i.e., gas-filled liposomes used as imaging agents) and a second different frequency can be used to burst the liposomal bubbles, as discussed further below.

In one embodiment, the liposomal imaging agent is bound to an antibody by an antigenic linker. Specifically, the antibody can be bound to an epitope that protrudes from the outer surface of the liposome. Examples of antibodies useful in connection with the present invention include polyclonal and monoclonal antibodies specific to infectious diseases and tumor antigens, cytokines, growth factors, immunoglobulin, matrix metalloproteases, amino acids, peptides, extracellular matrix proteins, purified neurochemicals, chemokines, fragments of RNA and DNA, and nucleic acids. Alternatively, a chelator may be used to bind other chemotherapeutic agents such as heparin or protamine.

The antibody targets the tumor or other target site, thereby binding the liposomal imaging agent to the target site. This mechanism better assures that the liposomal imaging agent will be in the desired location. Additionally, the use of antibodies permits smaller liposomes to bind to the target. All of these factors enhance the resulting ultrasound image.

Additionally, the catheter can be used to deliver liposomes containing therapeutic agents to the target site. The therapeutic agent-containing liposomes are preferably also bound to an antibody by a non-antigenic linker, as described above. If desired, one or more therapeutic agents can be incorporated into the same liposomes with the imaging agent or the different agents can be provided in different liposomes. Examples of suitable therapeutic agents for use in connection with the invention include trastuzumab (commercially available from Genentech under the name Herceptin®), infliximab (commercially available from Centocor under the name Remicade®), and abciximab (commercially available from Eli Lilly under the name ReoPro®).

When the imaging is finished, the catheter can then be used to break the linkage, for example, with radio frequency energy, to thereby release the liposomes so that they can pass through the patient's system and be released. Liposomes carrying therapeutic agents can be similarly broken down using the catheter.

The preceding description has been presented with reference to presently preferred embodiments of the invention. Workers skilled in the art and technology to which this invention pertains will appreciate that alterations and changes in the described methods may be practiced without meaningfully departing from the principal, spirit and scope of this invention.

What is claimed is:

1. A method for imaging diseased tissue, comprising:
   delivering to the diseased tissue a liposomal imaging agent comprising liposomes containing an imaging agent, the liposomal imaging agent being bound to an antibody by an antigenic linker, wherein the antibody binds the liposomal imaging agent to the diseased tissue;
   breaking the liposomes to release the imaging agent using a catheter; and
   viewing the imaging agent using an imaging technique.

2. The method according to claim 1, wherein the liposomal imaging agent is delivered to the diseased tissue using the catheter.

3. The method according to claim 1, wherein the liposomes are broken by applying radio frequency energy or ultrasound energy with the catheter.

4. The method according to claim 1, wherein the antibody is selected from the group consisting of polyclonal antibodies, monoclonal antibodies, cytokines, growth factors, immunoglobulin, matrix metalloproteases, amino acids, peptides, extracellular matrix proteins, purified neurochemicals, chemokines, RNA fragments, DNA fragments, and nucleic acids.

5. The method according to claim 1, wherein the liposomal imaging agent comprises gas-filled liposomes.

6. The method according to claim 5, wherein the gas-filled liposomes comprise at least one gas selected from the group consisting of air, oxygen, hydrogen, nitrogen, fluorocarbons, argon, xenon, helium, and fluoropropanes.

7. The method according to claim 5, wherein the gas-filled liposomes are prepared by:
   preparing liposomes comprising an inner retentate surrounded by one or more outer layers;
   freezing and thawing the liquid liposomes to induce the inner retentate to go directly from the solid state to the gaseous state while the one or more outer layers of the liposome do not.

8. The method according to claim 1, further comprising delivering energy directly into the diseased tissue using the catheter.

9. The method according to claim 8, wherein the energy is selected from radio frequency energy and ultrasound energy.

10. The method according to claim 1, further comprising, after viewing the imaging agent, breaking the antigenic linkage using the catheter to release the liposomes from the diseased tissue.

11. A method for imaging and treating diseased tissue comprising:
    imaging diseased tissue according to the method of claim 1, wherein the liposomes containing the imaging agent further contain a therapeutic agent; and
    breaking the liposomes to release the therapeutic agent to thereby treat the diseased tissue with the therapeutic agent.

12. The method according to claim 11, wherein the therapeutic agent is selected from the group consisting of trastuzumab, infliximab and abciximab.

13. A method for imaging and treating diseased tissue comprising:
    imaging diseased tissue according to the method of claim 1; and
    introducing a therapeutic agent to the diseased tissue using the catheter to thereby treat the diseased tissue.

14. The method according to claim 13, wherein the therapeutic agent is selected from the group consisting of trastuzumab, infliximab and abciximab.

15. The method according to claim 13, wherein the therapeutic agent is contained within liposomes.

16. The method according to claim 1, wherein the diseased tissue is selected from the group consisting of tumors, areas of infection, areas of infarction, areas of scarring, areas of degeneration, and areas of tissue overgrowth of unknown etiology.

* * * * *

UNITED STATES PATENT AND TRADEMARK OFFICE
CERTIFICATE OF CORRECTION

PATENT NO. : 6,979,296 B2 Page 1 of 1
APPLICATION NO. : 10/406748
DATED : December 25, 2005
INVENTOR(S) : See It is certified that error appears in the above-identified patent and that said Letters Patent is hereby corrected as shown below:

On the Title Page
Item
(75) Inventor           Delete "Jacko"
                        Insert --Jackie--

Signed and Sealed this

Seventeenth Day of October, 2006

JON W. DUDAS
*Director of the United States Patent and Trademark Office*

UNITED STATES PATENT AND TRADEMARK OFFICE
CERTIFICATE OF CORRECTION

PATENT NO. : 6,979,296 B2
APPLICATION NO. : 10/406748
DATED : December 27, 2005
INVENTOR(S) : See It is certified that error appears in the above-identified patent and that said Letters Patent is hereby corrected as shown below:

On the Title Page
Item
(75) Inventor                    Delete "Jacko"
                                 Insert --Jackie--

This certificate supersedes Certificate of Correction issued October 17, 2006.

Signed and Sealed this

Twenty-first Day of November, 2006

JON W. DUDAS
*Director of the United States Patent and Trademark Office*